(12) United States Patent
Grosbois et al.

(10) Patent No.: US 6,474,339 B1
(45) Date of Patent: Nov. 5, 2002

(54) DEVICE FOR PREVENTING SNORING AND APNOEA DURING SLEEP

(75) Inventors: Jacques Grosbois, Paray-Vieille-Poste; Christian Michaud, Annepont, both of (FR)

(73) Assignee: Aeroflux Medical International - AMI, Paris (FR)

( * ) Notice: Subject to any disclaimer, the term of this patent is extended or adjusted under 35 U.S.C. 154(b) by 0 days.

(21) Appl. No.: 09/254,204
(22) PCT Filed: Sep. 5, 1997
(86) PCT No.: PCT/FR97/01569
§ 371 (c)(1),
(2), (4) Date: Mar. 3, 1999
(87) PCT Pub. No.: WO98/09675
PCT Pub. Date: Mar. 12, 1998

(30) Foreign Application Priority Data

Sep. 5, 1996 (FR) .............................. 96 10827

(51) Int. Cl.[7] .................................................. A61F 5/56
(52) U.S. Cl. ......................... 128/848; 128/859; 602/902
(58) Field of Search ................ 128/846, 848, 128/859–862; 602/902

(56) References Cited

U.S. PATENT DOCUMENTS

| 2,882,893 A | * | 4/1959 | Godfroy | 128/861 |
|---|---|---|---|---|
| 3,057,347 A | | 10/1962 | McGee | |
| 4,222,378 A | | 9/1980 | Mahoney | |
| 4,270,531 A | * | 6/1981 | Blachly | 128/861 |
| 5,402,776 A | | 4/1995 | Islava | |
| 5,529,062 A | | 6/1996 | Byrd | |
| 5,533,523 A | * | 7/1996 | Bass | 128/859 |
| 5,988,170 A | * | 11/1999 | Thomas | 128/848 |

FOREIGN PATENT DOCUMENTS

| FR | 2 711 320 | 4/1995 |
|---|---|---|
| GB | 299457 | 10/1928 |

* cited by examiner

Primary Examiner—Michael A. Brown
(74) Attorney, Agent, or Firm—Young & Thompson

(57) ABSTRACT

The device is for suppressing snoring and apnoea during sleep. It is placed in the oro-pharynx and at the buccal cavity region during sleep. It comprises a flexible tube (1) arciform and transversally flattened, of adapted anatomical design, for being placed between the tongue (13) and the soft palate (15), down to at least the base of the tongue (14). A filter (2) is fixed to the external end of this tube. The filter can be removable. Thus, the air breathed in (10) moves freely from outside up to the larynx, without snoring or apnoea. A fixing system (24) is provided so that the tube is maintained well inside the mouth during sleep.

12 Claims, 4 Drawing Sheets

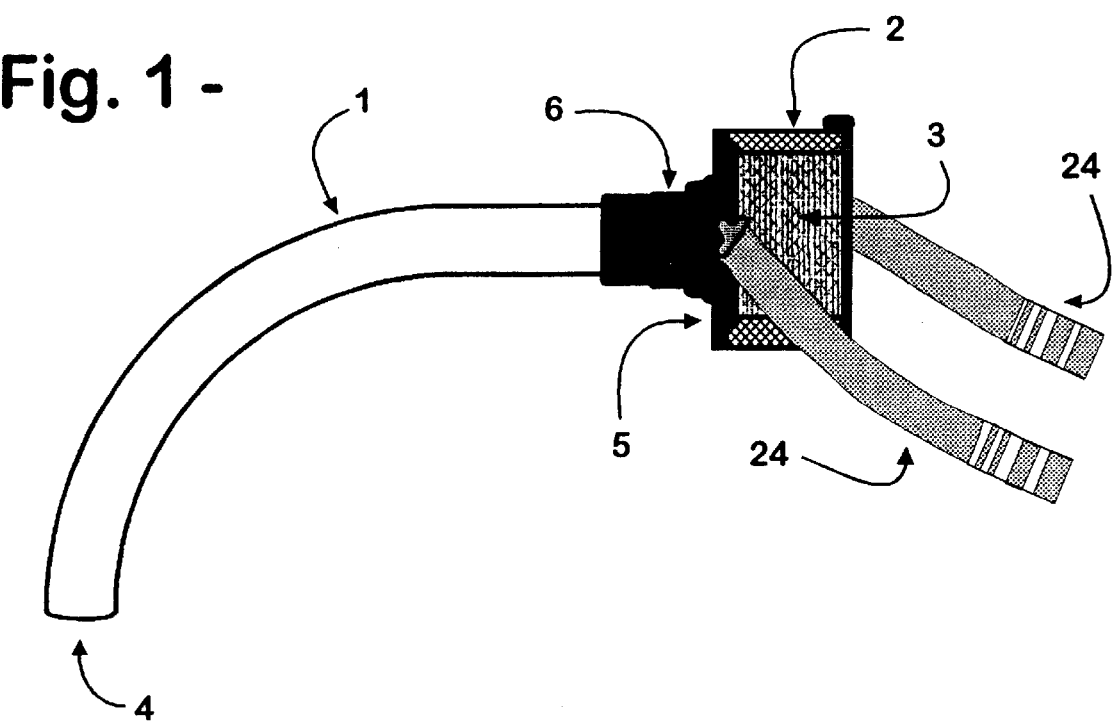
Fig. 1 -
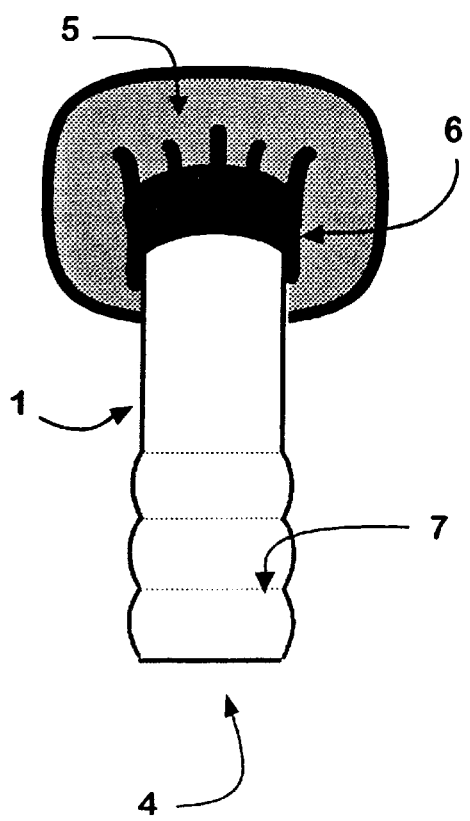
Fig. 2 -

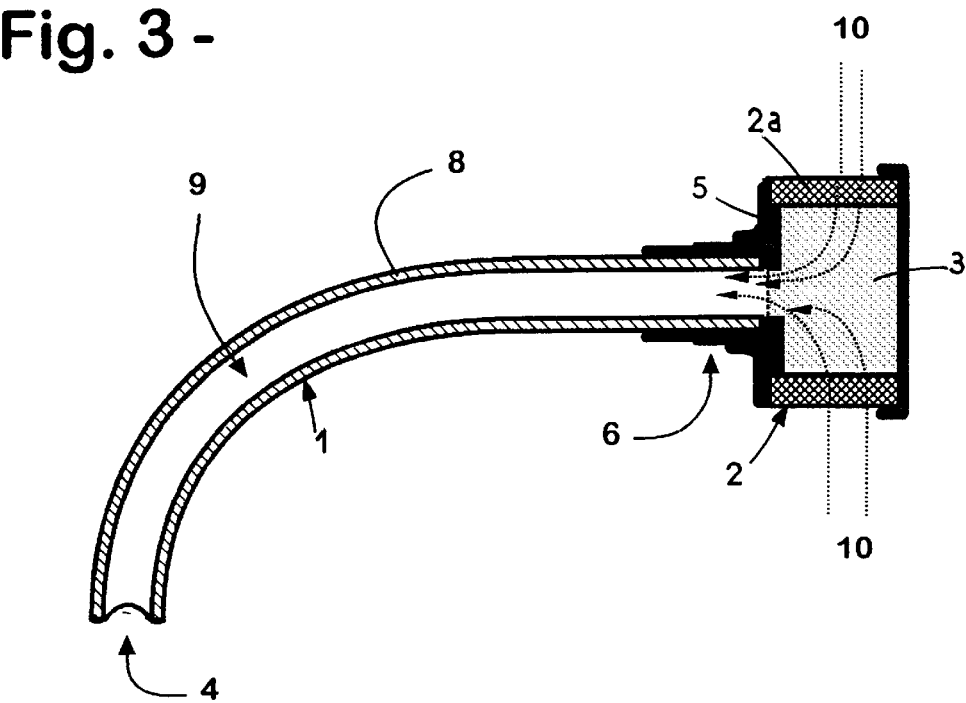
Fig. 3 -
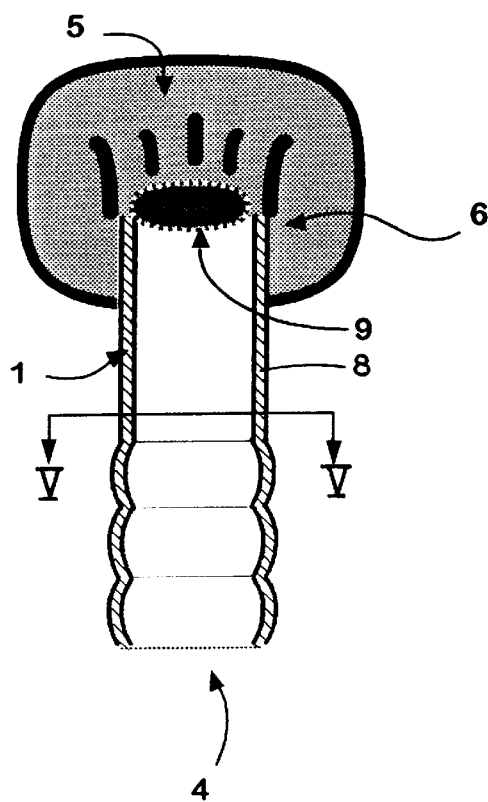
Fig. 4 -
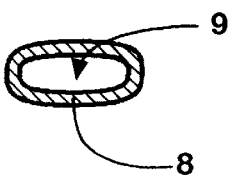
- Fig. 5 -

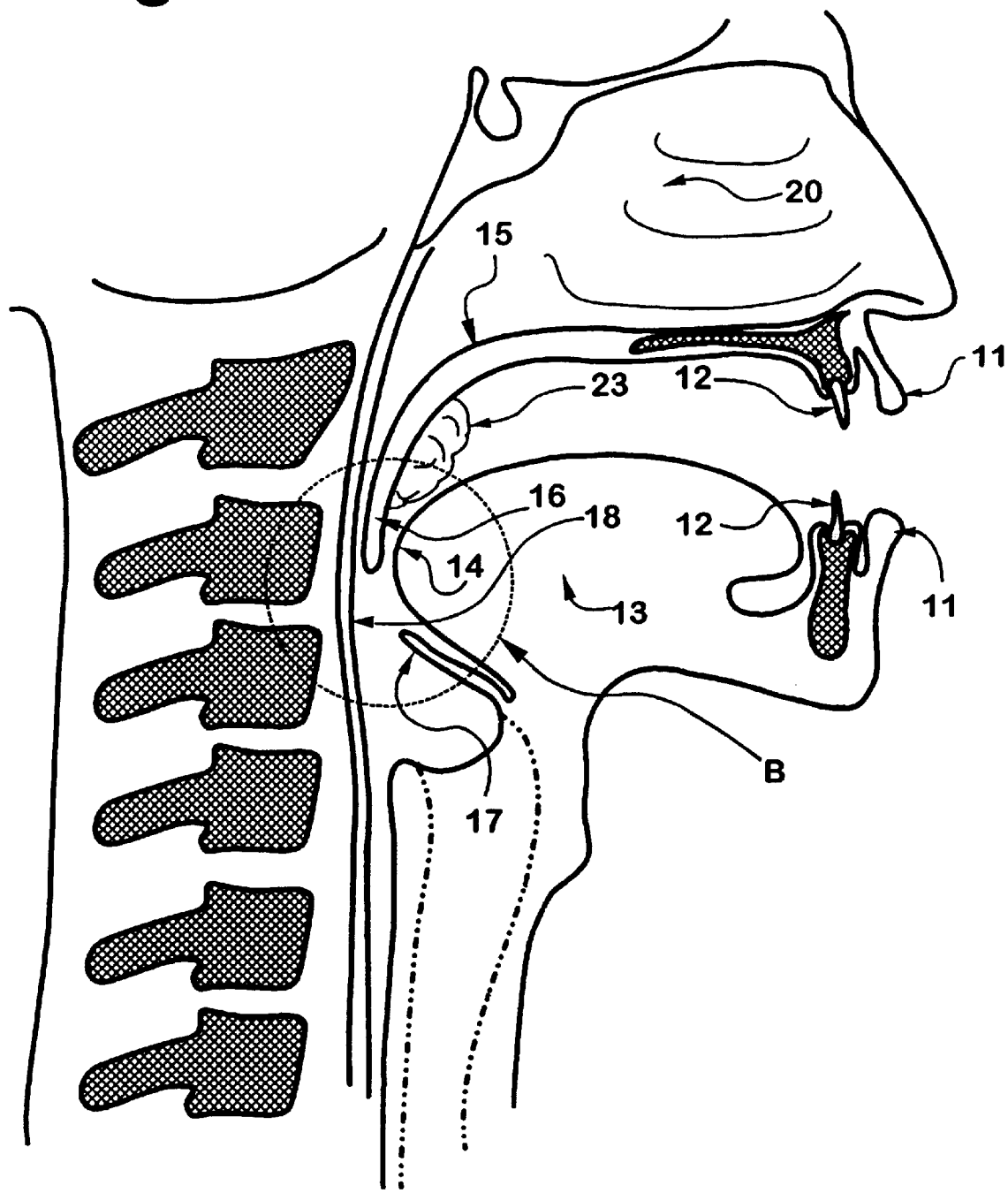
- Fig. 6 -

- Fig. 7 -
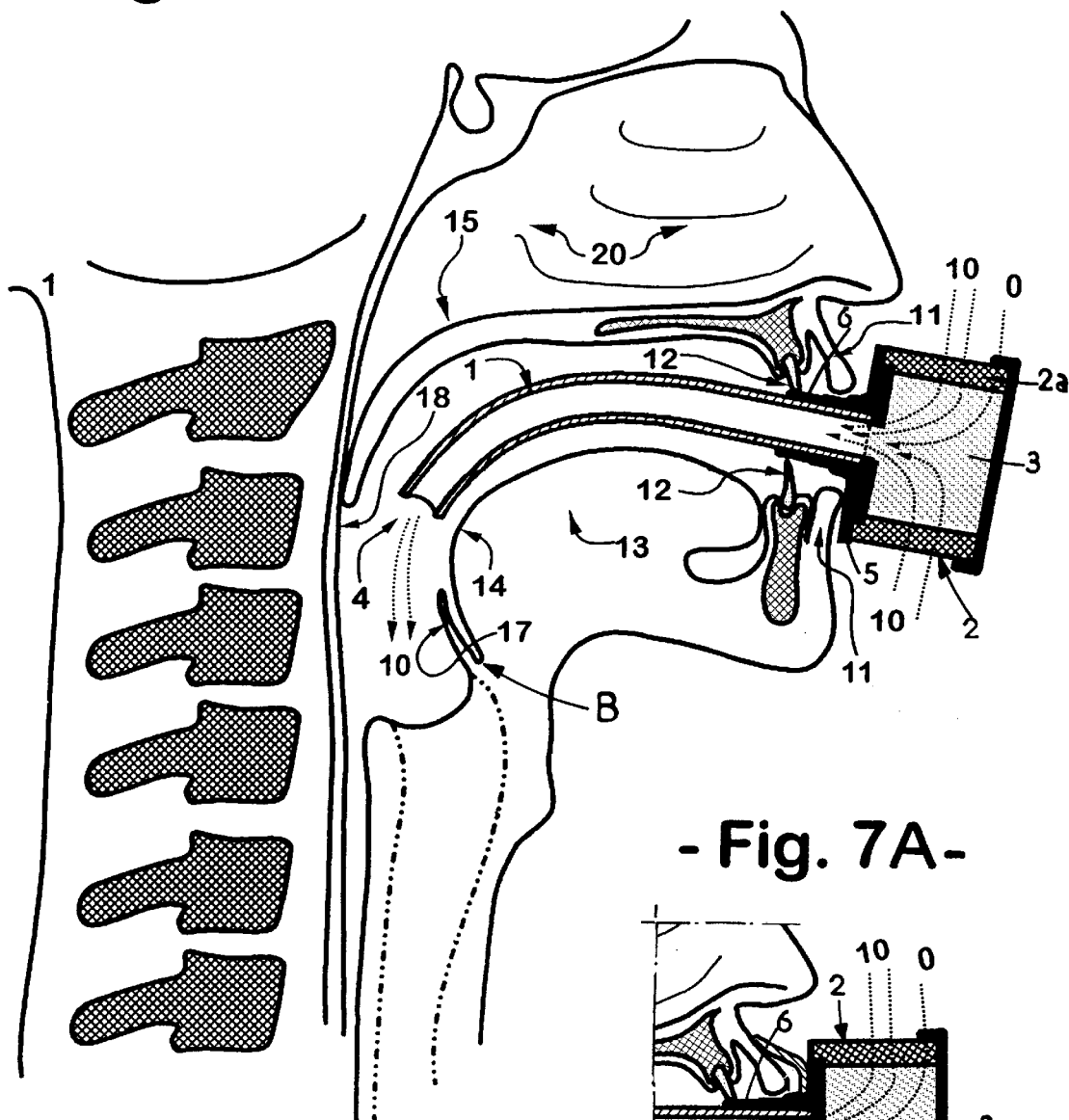
- Fig. 7A -
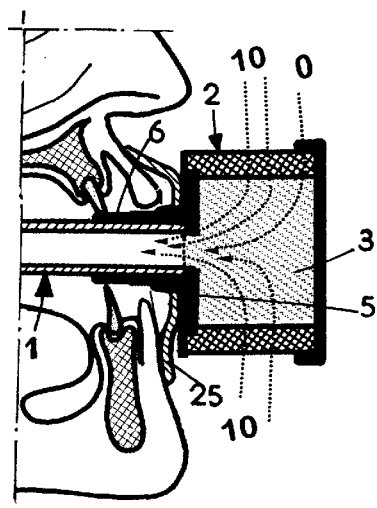

DEVICE FOR PREVENTING SNORING AND APNOEA DURING SLEEP

CROSS REFERENCE TO RELATED APPLICATION

This is the 35 USC 371 National Stage of International application PCT/FR97/01569 filed on Sep. 5, 1997, which designated the United States of America.

FIELD OF THE INVENTION

The invention concerns an intra-buccal-pharyngeal device for treating ronchopathy.

The invention is more particularly aimed at eliminating snoring and preventing sleep apnoea affecting some patients when sleeping.

BACKGROUND OF THE INVENTION

FIG. 6 of the accompanying drawings shows the relevant anatomy and is used to explain the mechanisms of snoring.

Snoring is a noise produced when breathing in, or predominantly when breathing in, by vibration of soft pharyngeal tissue.

The mechanism of snoring is not yet fully explained. Snoring could be the result of the interaction of a number of anomalies: local anatomical factors, abnormally collapsible pharyngeal walls, muscle tone problems and the like.

Many anomalies can constrict the upper respiratory tracts: nasal obstruction by deflection of the septum 20, macroglossia or hypertrophy of the tonsils 23, retro- or micrognathism.

In "benign" snoring the pharynx shrinks significantly. This reduction in the pharyngeal passage is due to an excessively long soft palate 15 and uvula 16, descending behind the base 14 of the tongue 13. Oscillation of these structures generates an audible vibration, snoring.

In heavy snorers, in addition to the noise, the increased pharyngeal resistance limits the flow on breathing in at various levels, in particular in the region of the soft palate 15 and the base 14 of the tongue 13 which are pressed against the posterior pharyngeal wall 18. Dorsal decubitus encourages snoring, perhaps because the tongue 13 drops back, but above all because the base of the tongue 14 presses against the posterior pharyngeal wall 18.

Snoring causes many problems. Apart from the nuisance to others, snoring causes impoverished sleep and reduces oxygenation of the blood to a greater or lesser extent, which can have harmful consequences for all of the organism. It appears that heavy snorers, more often than light snorers, are affected by arterial hypertension and cardiac ischaemic problems of the angina or myocardial infarctus type. They would also seem to have a predisposition to cerebral ischaemia.

Sleep apnoea syndrome (SAS) is a more severe form of snoring. It consists in heavy snoring associated with real apnoea, of greater or longer duration, but possibly lasting up to two minutes and repeating throughout the night, through total obstruction of the pharyngeal airway.

These interruptions of respiration cause successive awakenings (through the operation of the safeguard system) so that the pharyngeal muscles contract and allow air to pass into the lungs.

During the daytime the main symptom is drowsiness. It varies in severity, from the simple feeling of chronic fatigue to unintentional falling asleep during activity.

Various means have been invented and tried in order to reduce or even eliminate snoring: special pilows (international patent application WO-91/11157), "gadgets" preventing sleeping on the back, various medications, electronic systems for partially awakening the sleeper, intra-buccal devices for holding the jaws apart (patent application EP0599445 and international patent application WO-94/28832) or for pressing back the tongue (international patent applications WO-92/09249 and WO-96/25193), but in all cases without significant results.

More recently, and because of our better knowledge of mechanisms causing sounds during snoring, surgery of the pharynx has represented a notable advance in the treatment of these problems. In the case of SAS, respirators have been developed to insufflate air at a positive pressure (C.P.A.P.: "Continuous Positive Air Pressure") to prevent apnoea.

All prior art methods and devices are either ineffective or effective but costly and/or bulky and at least difficult for patients to use on themselves outside the hospital environment.

U.S. Pat. No. 3,057,347 describes a device for resuscitating patients suffering from respiratory arrest, for example after electrocution or drowning.

The device has a canula with a curved proximal part and a straight distal part, intended to be inserted as far as the base of the tongue and through the buccal cavity, respectively, projecting out of the buccal cavity so that a rescuer can insufflate air. The distal part has a support disc radially around it and which rests on the lips of the patient to position the assembly correctly. A filter in the distal part of the canula prevents moisture insufflated with the air breathed out by the rescuer from reaching the respiratory tracts of the patient. The canula is made from a semi-rigid elastic material so that it can adapt to the particular anatomical conformation of each patient. Application of the above device is exclusively reserved to resuscitation of patients and the device is intended in particular to create a non-obstructed passage between the mouth of the rescuer and the respiratory tracts downstream of the base of the tongue (larynx and trachea). Because the patient is unconscious, the canula must have sufficient rigidity to be inserted, possibly forcibly inserted, as the pharyngeal muscles may have become tetanized because of the trauma.

SUMMARY OF THE INVENTION

The aim of the present invention is to propose a simple and effective device for treating ronchopathy and sleep apnoea, which avoids all the drawbacks of previously used devices and methods, surgical or otherwise, the device being particularly convenient to use and easily fitted by a patient suffering from ronchopathy and/or sleep apnoea.

The invention therefore consists in a device for treating ronchopathy and sleep apnoea adapted to be placed in the oro-pharynx and in the pre-buccal region, characterized in that it comprises in combination:

an anatomical shape curved tube having a length such that in situ its proximal end reaches at least the base of the tongue and its distal end projects out of the buccal cavity, and reinforcing means near said distal end and adapted to reinforce said tube in the area of the teeth and the lips to prevent crushing said tube, so that, placed in the oro-pharynx of a patient while sleeping, the airflow produced by the patient can pass freely and without obstacle between the outside and the area downstream of the base of the tongue, without blockage and without causing vibration of surrounding soft tissue, in particular the soft palate, the base of the tongue and the pharyngeal wall.

BRIEF DESCRIPTION OF THE DRAWINGS

Other features and advantages of the invention will become apparent in the course of the following description given by way of example only and with reference to the appended drawings, in which:

FIG. 1 shows the device in accordance with the invention in profile;

FIG. 2 shows the device in accordance with the invention from the front, at the proximal end;

FIG. 3 shows the device in accordance with the invention in profile and in section;

FIG. 4 shows the device in accordance with the invention from the front and in section;

FIG. 5 shows a cross section of the tube of the device of the invention;

FIG. 6 shows an anatomic section of the oro-pharynx;

FIG. 7 shows the device in place in the oro-pharynx and in the pre-buccal region; and FIG. 7A is a partial view of a variant of the device in accordance with the invention in the pre-buccal region.

DETAILED DESCRIPTION OF THE INVENTION

Referring to the drawings, in accordance with a first feature of the invention the device includes an intra-buccal-pharyngeal tube 1 which is flexible and not rigid, so that it can be better tolerated by the patient when fitted before going to sleep and while sleeping. The tube 1 is of appropriate anatomical shape, i.e. arc-shape to fit between the tongue 13 and the soft palate 15, to permit the passage of air.

The flexible, non-rigid material of the tube must be compatible with contact with the buccal mucous membrane. It must be of suitable flexibility so that the walls between which it is inserted do not collapse due to the pressure of the tissue of the soft palate and the tongue.

It is important for the tube to be deformable to some extent, but that it resume an arc-shape when the deforming force is removed. Also, the passage delimited by the tube in situ must also remain open, in particular at its proximal end.

Given the above considerations, the tube 1 is preferably made of a material having a Shore hardness in the range 10 to 50, and silicone or latex may be suitable.

The wall 8 of the tube 1 varies in thickness depending on the material used, and is approximately 2 mm, for example, but the thickness can vary in accordance with the required hardness.

A particularly appropriate material is a flexible food grade silicone that can be polymerized at ambient temperature, such as Rhône-Poulenc Silbione RTV 71557®. Flexible materials other than silicone or latex can be used provided that they have the specified hardness, are not irritating to the skin or the mucous membranes and have no toxic effect on the organism.

The tube 1 can be formed by depositing silicone on a pre-formed mould, but other manufacturing methods are possible, in particular injection moulding.

Because of the flexible tube 1, the inspired air 10 can therefore pass freely from the outside to the larynx, bypassing the obstacle in the area B (FIG. 7) constituted by the tongue 13, the soft palate 15 and the base 14 of the tongue. There is therefore no impediment to the passage of air and so snoring is eliminated, and likewise apnoea.

Recent research and the unsatisfactory results of soft palate surgery tend to show that the obstacle to the flow of air responsible for vibration of the soft tissue or for complete obstruction of the airway is located in area B (FIG. 6) where there come together and collapse the soft palate 15, the uvula 16, the base of the tongue 14, against the posterior pharyngeal wall 18, and the tonsils 23, which reduce the width of the pharynx.

The device in accordance with the invention provides an air passage avoiding the anatomical obstacles in area B which collapse during sleep. The flow of air 10 therefore reaches the larynx without impediment and without noise.

In accordance with another feature of the invention, an extra-buccal base 5 bears against the teeth 12 and the lips 11. The first few distal centimeters of the tube 1 are strengthened by a portion 6 in the form of a bush or reinforcement made from a material other than that of the tube 1 to increase its rigidity where the teeth 12 bear on it. The teeth bear on the reinforcement 6 which flares outwards towards the distal end, and the extra-buccal base 5 rests on the lips 11. The base 5 and the reinforcement 6 can be made of ABS (Acrylonitrile-Butadiene-Styrene), polystyrene or another similar material. A metal such as aluminum or titanium can equally be used.

In accordance with another important feature of the invention a filter 2 with sufficient filter surface area is disposed at the distal end of the tube 1 in order to filter and humidify the air inhaled through a filter part 3 of an appropriate material. The filter is attached to the base 5 by any appropriate means. It is essential to replace the nasal function by removing particles in suspension from the air, moistening it and warming it. In the absence of any such filter, the air would rapidly dry out the laryngeal and tracheal mucous membrane and the device would not be well tolerated. Dust inhaled during sleep would also be a factor in low tolerance of the device by causing irritation and coughing.

The filter can take various forms and be constructed of various materials. In this embodiment it comprises an air-permeable annular cage 2a in which the filter part 3 is placed. The filter part can be a loose mesh synthetic foam, such as a PVC (Poly Vinyl Chloride) foam, or sheets of agglomerated polyamide or polyester fibres, but other materials can be used provided that they do not impede the flow of air 10. This precludes installation inside the tube 1 (as in the device from the aforementioned Us patent). The filter part 3 is preferably removable for cleaning or changing it. The cage 2a can be made of ABS, like the base 5 and the reinforcement 6.

A system for fixing the filter 2 to the tube 1 can equally be provided so that all of the filter can be changed, the filter then being fixed or removable.

In the embodiment shown the main tube 1 has an oval shape in cross section (FIG. 5) with outside dimensions of 20 mm wide by approximately 10 mm high. The internal aperture 9 is 16 mm wide and approximately 6 mm high. The dimensions can differ according to the size of the tube and the material used for it. The flattened or oval section provides a passage 9 and therefore an air flowrate that are sufficient, without impeding the flow of air 10, so that the flow is silent and the device is well tolerated during sleep. Note that in FIG. 7 the dimensions of the tube 1 relative to the anatomy of the person are not to scale, in order to make the operation of the device clear. This is clear on comparing FIG. 6 with FIG. 7.

The length of the tube 1 can be adapted to suit each patient by simply cutting off the proximal end 4 of the tube 1 so that the proximal orifice does not abut against the epiglottis 17, which could cause pain or reflex nausea or coughing. Accordingly, the end 4 of the tube 1 must be easily cut with simple scissors. To facilitate this cutting, in this embodiment, the proximal end 4 of the tube 1 has notches, projections or special marks 7 (FIG. 2) to specify and facilitate cutting, so that the length can be adapted progressively.

The wall 8 of the tube 1, the base 5 and the reinforcement 6 of the tube 1 can be reinforced with another material, metal or synthetic, to increase its rigidity, for example wires, plates or other materials. It can be an internal reinforcement in the wall 8, the base and/or the reinforcement 6, or outside them.

A fixing system is desirable to hold the device in the oro-pharynx during sleep. The simplest system uses one or more elastic bands 24 passing behind the ears, the head or the neck.

FIG. 7A shows a variant of the device in accordance with the invention in which a cap 25 is threaded over the reinforcement 6 against the base 5. The cap is made from a flexible material, for example the same as that of the tube, and when unstressed has a more or less conical shape with the convex side facing towards the distal end of the tube 1. The cap 25 is pressed against the outside of the lips, deforming when the device is put into place, so creating a seal preventing saliva flowing out at the interface between the base 5 and the outlet of the buccal cavity.

What is claimed is:

1. Device for treating ronchopathy and sleep apnoea adapted to be placed in the oro-pharynx and in the pre-buccal region of a patient while sleeping, which comprises in combination:

an anatomical shaped curved tube having a length such that in situ its proximal end reaches at least the base of the tongue and its distal end projects out of the buccal cavity;

reinforcing means fixed to said tube near said distal end adapted to reinforce said tube in the area of the teeth and the lips and to prevent crushing said tube;

a buccal base integral with said reinforcing means and adapted to bear against an external face of the lips; the base and said reinforcing means being made of a material having a hardness greater than that of the material of the tube to increase its rigidity where the teeth bear on it;

so that, placed in the oro-pharynx of the patient while sleeping, airflow produced by the patient can pass freely and without obstacle between the outside and the area downstream of the base of the tongue, without blockage and without causing vibration of surrounding soft tissue including the soft palate, the base of the tongue and the pharyngeal wall.

2. The device according to claim 1, further comprising a filter attached to said base in order to filter and humidify inhaled air.

3. The device according to claim 2, wherein the filter is fixed or removable.

4. The device according to claim 1, wherein the tube has a flattened section to provide a passage and therefore an airflow rate that are sufficient, without impeding the flow of aspirated air, so that the flow is silent and the device is well tolerated during sleep.

5. The device according to claim 1, wherein the length of the tube can be adapted to suit each patient by simply cutting off its proximal end.

6. The device according to claim 5, wherein the proximal end of the tube has notches, projections or special marks to specify and facilitate cutting.

7. The device according to claim 1, wherein the tube is made of a flexible, non-rigid material that is non-irritant to the skin and the mucous membranes and non-toxic to the patient, said tube having a Shore hardness ranging from 10 to 50.

8. The device according to claim 7, wherein the material of said tube is silicone or latex.

9. The device according to claim 1, wherein the wall of the tube is reinforced with another material to modify its rigidity.

10. The device according to claim 1, further comprising a fixing system comprised of elastic bands attached to said base and adapted to be passed behind the ears, the head or the neck of the patient in order to hold the device in the oro-pharynx during sleep.

11. The device according to claim 1, further comprising a cap positioned on said tube around the reinforcing means to form a seal at the lips and prevent outflow of saliva.

12. Device for treating ronchopathy and sleep apnoea adapted to be placed in the oro-pharynx and in the pre-buccal region of a patient while sleeping, which comprises in combination:

an anatomical shaped curved tube having a length such that in situ its proximal end reaches at least the base of the tongue and its distal end projects out of the buccal cavity; the length of the tube being adapted to suit each patient by simply cutting off its proximal end which has notches, projections or special marks to specify and facilitate cutting; and reinforcing means near said distal end adapted to reinforce said tube in the area of the teeth and the lips and to prevent crushing said tube;

so that, placed in the oro-pharynx of the patient while sleeping, airflow produced by the patient can pass freely and without obstacle between the outside and the area downstream of the base of the tongue, without blockage and without causing vibration of surrounding soft tissue including the soft palate, the base of the tongue and the pharyngeal wall.

* * * * *